(12) United States Patent
Chen et al.

(10) Patent No.: US 9,265,918 B2
(45) Date of Patent: Feb. 23, 2016

(54) MULTILAYER MEDICAL BALLOON

(75) Inventors: John J. Chen, Plymouth, MN (US); Daniel J. Horn, Shoreview, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1457 days.

(21) Appl. No.: 12/203,473

(22) Filed: Sep. 3, 2008

(65) Prior Publication Data

US 2010/0057001 A1    Mar. 4, 2010

(51) Int. Cl.
*A61M 29/00* (2006.01)
*A61M 25/10* (2013.01)
*A61L 29/06* (2006.01)
*A61L 29/08* (2006.01)
*A61L 29/14* (2006.01)

(52) U.S. Cl.
CPC ........... *A61M 25/1011* (2013.01); *A61M 25/10* (2013.01); *A61L 29/06* (2013.01); *A61L 29/08* (2013.01); *A61L 29/14* (2013.01)

(58) Field of Classification Search
CPC ........... A61M 25/10; A61M 25/1011; A61M 2025/1075; A61M 5/2459; A61L 29/06; A61L 29/08; A61L 29/14
USPC ............... 604/96.01, 101.02, 103.11, 103.12, 604/103.13, 912, 915, 103.05, 3.06, 917–1; 606/198
See application file for complete search history.

(56) References Cited

U.S. PATENT DOCUMENTS

| | | | |
|---|---|---|---|
| 4,528,346 A * | 7/1985 | Sugie et al. | 525/523 |
| 4,906,244 A | 3/1990 | Pinchuk et al. | |
| 5,108,415 A | 4/1992 | Pinchuk et al. | |
| 5,156,612 A | 10/1992 | Pinchuk et al. | |
| 5,195,969 A | 3/1993 | Wang et al. | |
| 5,236,659 A | 8/1993 | Pinchuk et al. | |
| 5,270,086 A | 12/1993 | Hamlin | |
| 5,290,306 A | 3/1994 | Trotta et al. | |
| 5,304,197 A | 4/1994 | Pinchuk et al. | |
| 5,356,591 A | 10/1994 | Pinchuk et al. | |
| 5,403,292 A | 4/1995 | Ju | |
| 5,447,497 A | 9/1995 | Sogard et al. | |
| 5,449,371 A | 9/1995 | Pinchuk et al. | |
| 5,478,320 A | 12/1995 | Trotta | |
| 5,490,839 A | 2/1996 | Wang et al. | |
| 5,509,899 A * | 4/1996 | Fan et al. | 604/103.14 |
| 5,556,383 A | 9/1996 | Wang et al. | |
| 5,587,125 A | 12/1996 | Roychowdhury | |

(Continued)

FOREIGN PATENT DOCUMENTS

EP    0768097    4/1997
JP    2002543893    12/2002

(Continued)

OTHER PUBLICATIONS http://www.calce.umd.edu/general/Facilities/Hardness_ad_.htm.

(Continued)

*Primary Examiner* — Quynh-Nhu H Vu
(74) *Attorney, Agent, or Firm* — Seager, Tufte & Wickhem, LLP

(57) ABSTRACT

An expandable medical balloon including an inner layer formed of a poly(ether-block-amide) copolymer and an outer layer formed of a polyamide, the expandable medical balloon having a burst strength of greater than 50,000 psi, and to methods of making and using the same.

19 Claims, 4 Drawing Sheets

(56) References Cited

U.S. PATENT DOCUMENTS

| | | |
|---|---|---|
| 5,613,979 A | 3/1997 | Trotta et al. |
| 5,620,649 A | 4/1997 | Trotta |
| 5,643,279 A | 7/1997 | Trotta |
| 5,693,034 A | 12/1997 | Buscemi et al. |
| 5,738,653 A | 4/1998 | Pinchuk et al. |
| 5,755,690 A | 5/1998 | Saab |
| 5,797,877 A | 8/1998 | Hamilton et al. |
| 5,830,182 A | 11/1998 | Wang et al. |
| 5,879,369 A | 3/1999 | Ishida |
| 5,913,861 A | 6/1999 | Trotta |
| 5,948,345 A | 9/1999 | Patel et al. |
| 5,951,941 A | 9/1999 | Wang et al. |
| 6,059,751 A | 5/2000 | Ostapchenko et al. |
| 6,086,556 A | 7/2000 | Hamilton et al. |
| 6,110,142 A | 8/2000 | Pinchuk et al. |
| 6,124,007 A | 9/2000 | Wang et al. |
| 6,146,356 A | 11/2000 | Wang et al. |
| 6,171,278 B1 | 1/2001 | Wang et al. |
| 6,328,925 B1 | 12/2001 | Wang et al. |
| 6,406,457 B1 | 6/2002 | Wang et al. |
| 6,500,146 B1 | 12/2002 | Pinchuk et al. |
| 6,500,148 B1 | 12/2002 | Pinchuk et al. |
| 6,547,768 B2 | 4/2003 | Trotta |
| 6,896,842 B1 | 5/2005 | Hamilton et al. |
| 6,946,092 B1 | 9/2005 | Bertolino et al. |
| 6,951,675 B2 | 10/2005 | Chin et al. |
| 7,101,597 B2 | 9/2006 | Wang et al. |
| 7,108,826 B2 | 9/2006 | Wang et al. |
| 7,128,862 B2 | 10/2006 | Wang |
| 7,163,522 B1 | 1/2007 | Wang et al. |
| 7,396,582 B2 * | 7/2008 | Claude et al. ............ 428/220 |
| 2005/0043679 A1 | 2/2005 | Devens, Jr. et al. |
| 2007/0142772 A1* | 6/2007 | Deshmukh et al. ...... 604/103.06 |

FOREIGN PATENT DOCUMENTS

| | | |
|---|---|---|
| JP | 2005319289 | 11/2005 |
| WO | 9913924 | 3/1999 |
| WO | 2006126311 | 11/2006 |
| WO | 2007120323 | 10/2007 |

OTHER PUBLICATIONS http://www.pebax.com/sites/pebax/en/properties/mechanical_properties1.page.

* cited by examiner

MULTILAYER MEDICAL BALLOON

FIELD OF THE INVENTION

The present invention relates to the field of expandable medical balloons, particularly those balloons employed for dilatation and for the delivery of medical devices.

BACKGROUND OF THE INVENTION

Expandable medical balloons are employed in a variety of medical procedures including plain old balloon angioplasty (POBA) as well as for delivery of medical devices to the treatment site such as stent delivery.

Medical applications wherein a balloon is employed intraluminally such as for POBA and stent delivery can be demanding applications due to the extremely small vessels, and the tortuous and long distances the catheter may travel to the treatment site. For such applications, it is typically desirable that the balloon be thin walled, while maintaining high strength as most commonly measured by hoop strength or pressure at burst, be relatively inelastic, and have predictable inflation properties.

Inelasticity is desirable to allow for easy control of the diameter, but some elasticity is desirable to enable the surgeon to vary the balloon's diameter as required to treat individual lesions. Suitably, small variations in pressure should not cause wide variation in balloon diameter.

It can be difficult to achieve an excellent balance of properties with a single polymer material. Therefore, a variety of polymer blends and multiple layer polymer balloons have been developed over the years.

There remains a need in the art, however, for an expandable medical balloon having an excellent balance of physical properties.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

In one aspect, the present invention relates to an expandable medical balloon having at least two layers, an inner layer formed from a softer, elastic material, and an outer layer formed from a harder, less elastic material.

In one aspect, the present invention relates to an expandable medical balloon having an inner layer formed of a polymer material having a Shore D hardness of about 25 to about 70 and an outer layer formed of a polymer material having a Rockwell hardness of about 60 to about 115, the expandable medical balloon having a burst strength of greater than 45,000 psi, more suitably greater than 47,500 psi and most suitably greater than 50,000 psi.

In one embodiment, the present invention relates to an expandable medical balloon including an inner layer formed of a poly(ether-block-amide) copolymer and an outer layer formed of a polyamide, the expandable medical balloon having a burst strength of greater than 45,000 psi, more suitably greater than 47,500 psi and most suitably greater than 50,000 psi.

In another aspect, the present invention relates to a method of making an expandable medical balloon, the method including forming a tubular parison, the tubular parison including an inner layer formed of a poly(ether-block-amide) copolymer and an outer layer formed from a polyamide, stretching said tubular parison at a stretch ratio of less than 4.0, radially expanding said tubular parison in a balloon mold and heat setting said balloon at a temperature of less than 150° C.

A synergistic increase in hoop strength has been exhibited with the dual layer balloons according to the invention.

These and other aspects, embodiments and advantages of the present invention will be apparent to those of ordinary skill in the art upon review of the Detailed Description and Claims to follow.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The present invention relates to an expandable medical balloon having at least two layers, an inner softer, more elastic layer, and an outer harder, less elastic layer. Suitably, the softer, more elastic inner layer is formed from a material which also has a lower tensile set (see ASTM D412). This lower tensile set material forming the inner layer provides for improved refoldability making withdrawal easier after a procedure is complete.

Suitably, the shore D hardness of the inner layer is less than about 75D, more suitably less than about 70D, with a range of about 25D to about 75D, more suitably about 25D to about 70D. In some embodiments, the range is about 50D to about 75D, more suitably 50D to about 70D.

Figure 1:
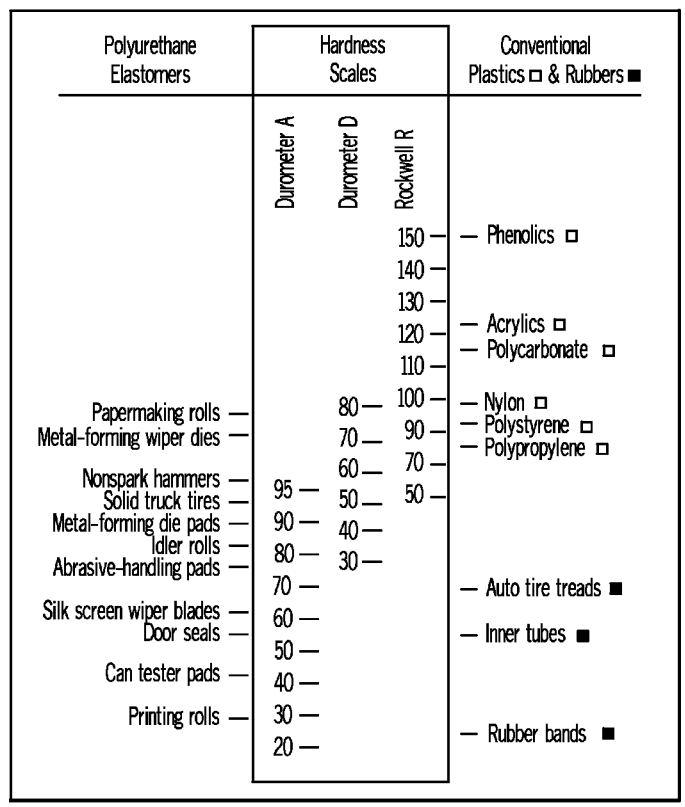
FIG. 1 is a table including a comparison of Rockwell hardness scale, Shore A hardness scale and Shore D hardness scale.

Suitably, the outer layer is harder than the inner layer. The outer layer may have a Rockwell hardness between about 60 and about 115, more suitably about 70 to about 115, and most suitably about 80 to about 115, although this range may vary. The Shore D hardness (ASTM D2240) of the outer layer is suitably greater than about 70D, more suitably greater than about 75D, and most suitably greater than about 80D. A comparison of Shore A, Shore D and Rockwell hardness is shown in FIG. 1. FIG. 1 is reproduced from http://www.calce.umd.edu/general/Facilities/Hardness_ad_.htm. As can be seen from the scale, nylon has a Shore D harness of 80 or greater and a Rockwell hardness of greater than about 95. These numbers are approximated from the scale.

In one embodiment, the inner layer is a poly(ether-block-amide) and the outer layer is nylon. In a preferred embodiment, the outer layer is nylon 12, formed from laurolactam.

Nylon 12 is available from Degussa-Hüls AG, North America under the tradename of Vestamid® L2101F. Degussa's national headquarters are located in Düsseldorf, Germany. Nylon 12 is available from a variety of polymer manufacturers. Poly(ether-block-amide) copolymers are available from Arkema, North America under the tradename of Pebax®. Arkema's headquarters are located in Philadelphia, Pa. Specific grades of Pebax® useful herein include, but are not limited to, 6333 and 7033, with 7033 being preferred.

In a preferred embodiment, the balloon is formed with only the inner and outer layer as described herein. The inner layer provides at least 10%, and in some embodiments at least 20% of the burst strength of the balloon. Optionally, a lubricious coating may be disposed on the outer layer. The lubricious coating does not provide structural integrity to the balloon.

Shore D hardness values of PEBAX® 6333, 7033 and 7233 can be found at http://www.pebax.com/sites/pebax/en/properties/mechanical_properties1.page and are reproduced below in table 1. The standard used for these measurements was ISO 868, which is equivalent to ASTM standard D2240.

TABLE 1

| Pebax ® Grade | Shore A Hardness Instantaneous | After 15 s | Shore D Hardness Instantaneous | After 15 s |
|---|---|---|---|---|
| 4033 | 90 | 89 | 41 | 34 |
| 5533 | — | — | 54 | 50 |
| 6333 | — | — | 64 | 58 |
| 7033 | — | — | 69 | 61 |
| 7233 | — | — | 69 | 61 |

Other materials such as polyurethane elastomers, for example Tecothane® polyurethanes available from Noveon, Inc. in Cleveland, Ohio, find utility for use as the inner, softer layer. A specific example is Tecothane® TT-1074A.

The resultant balloons suitably have a burst pressure of greater than about 400 psi, more suitably greater than about 450 psi, or a calculated burst strength of greater than 45,000 psi, more suitably greater than 47,500 psi and most suitably greater than 50,000 psi. Burst strength is sometimes referred to in the art as hoop strength or radial tensile strength.

The balloon may be formed using any suitable method known in the art. In some embodiments, the method suitably includes forming a tubular parison, stretching the tubular parison, placing the balloon parison in a balloon mold, and forming a balloon by radially expanding the tubular parison into the balloon mold. The balloon is then heat set. Balloon forming with stretching and radial expansion is disclosed in U.S. Pat. Nos. 5,913,861, 5,643,279 and 5,948,345, and in commonly assigned U.S. Pat. Nos. 6,946,092 and 7,1010, 597, each of which is incorporated by reference herein in its entirety.

The tubular parison may be formed using coextrusion techniques. The tubular parison may have two layers including a soft inner layer and a harder outer layer, or may have alternating soft and hard layers. For example, layers 1, 3 and 5 (with 1 being the innermost layer of the balloon) are formed from the flexible, softer layer, while layers 2, 4 and 6 are formed of the harder, higher strength polymer material.

Alternatively, the softer, more flexible inner layer can be coated either on the balloon parison, or on the balloon itself after it has been formed from the balloon parison. Coating can be accomplished out of a solvent or solvent blend. The coating can be injected into the tubular parison or balloon, for example.

In some embodiments, it may be desirable for the waist portion of the balloon to be formed of only a single layer. The waist can be masked with an inserted tube, or cleaned after application of the coating.

Suitably, the tubular parison is axially (longitudinally) stretched using a stretching ratio of less than 4.0X where X is the starting length of the tubular parison. In one specific embodiment, the method includes stretching the balloon parison at a ratio of 3.50X wherein X is the starting length of the tubular parison.

At a stretch ratio of significantly more than this, for example, at a stretch ratio of 4.25, a decrease in balloon burst pressure of more than 20% was observed, and the corresponding decrease in calculated burst strength was greater than 10%.

The balloon can then be formed from the tubular parison using any suitable technique including molding. Using molding techniques, the tubular parison can be placed into a mold and radially expanded. Molding pressures may range between about 500 psi and about 600 psi.

Suitably, the balloon is heat set at a temperature of about 150° C. or less. In some embodiments, the heat set temperature is about 125° C. or less. In a specific embodiment, the balloon is heat set at 120° C. It has been found that using a temperature for heat setting that is significantly higher than this, negatively impacts the ultimate burst strength of the balloon. For example, at a heat set temperature of 140° C., the burst pressure was found to decrease by more than 15% over the same balloon formed at 120° C., and the corresponding decrease in burst strength was more than 10%.

The resultant balloons, for example, those used for cardiovascular procedures, suitably have a wall thickness of between about 10 microns and about 30 microns, and even more suitably about 10 microns to about 20 microns.

Figure 2:
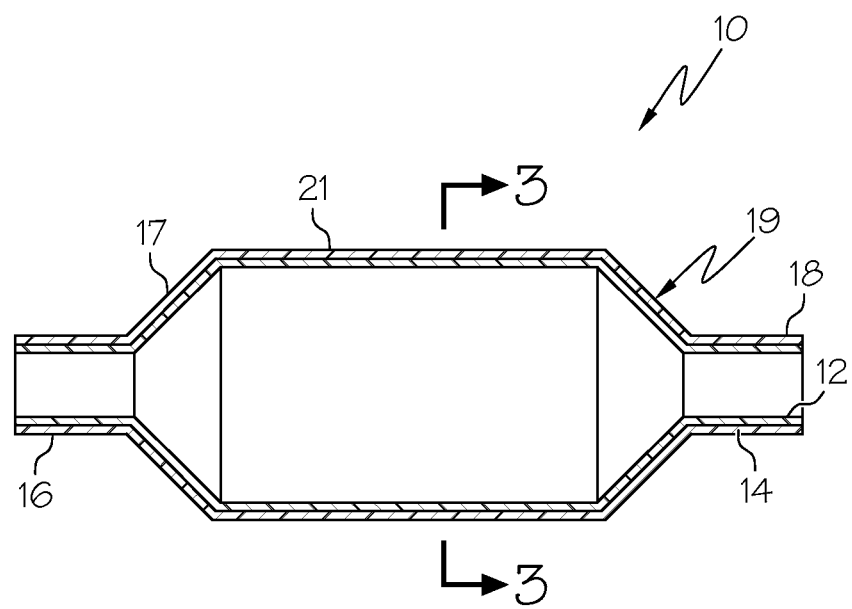
FIG. 2 is a longitudinal cross-section of a balloon having a dual-layer coating according to the invention
Figure 3:
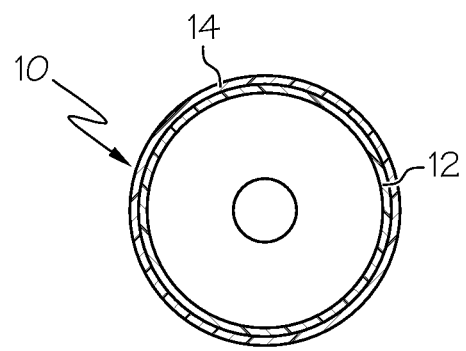
FIG. 3 is a radial cross-section taken at section 3-3 in FIG. 2.

Turning now to the figures, FIG. 2 is a longitudinal cross-sectional representation of a balloon 10 according to the invention. Balloon 10 is shown with dual layers having an inner layer 12 and an outer layer 14 in accordance with the invention. FIG. 3 is a radial cross-section taken at section 3-3 in FIG. 2.

The balloon can further include a lubricious coating (not shown). The lubricious coating may be applied to the balloon waists 16, 18, balloon cones, 17, 19 and balloon body 21, or any portion thereof. Suitably, lubricious coatings are applied at a thickness of about 0.1 microns to about 5.0 microns, more suitably about 0.5 microns to about 2.0 microns.

Any suitable lubricious material may be employed in the lubricious coating. Such lubricious coatings are known in the art. Examples of materials that can be used in the lubricious coatings include both thermoplastic and thermoset materials. The lubricious polymers can be either hydrophobic or hydrophilic. Hydrophilic materials are often preferred because they are typically more biocompatible. Lubricious coatings are disclosed in commonly assigned U.S. Pat. No. 5,509,899, the entire content of which is incorporated by reference herein.

Interpenetrating polymer networks can also be employed. These materials are described, for example, in commonly assigned U.S. Pat. No. 5,693,034, the entire content of which is incorporated by reference herein.

Coatings for the controlled delivery of therapeutic agents may also be optionally added.

Figure 4:
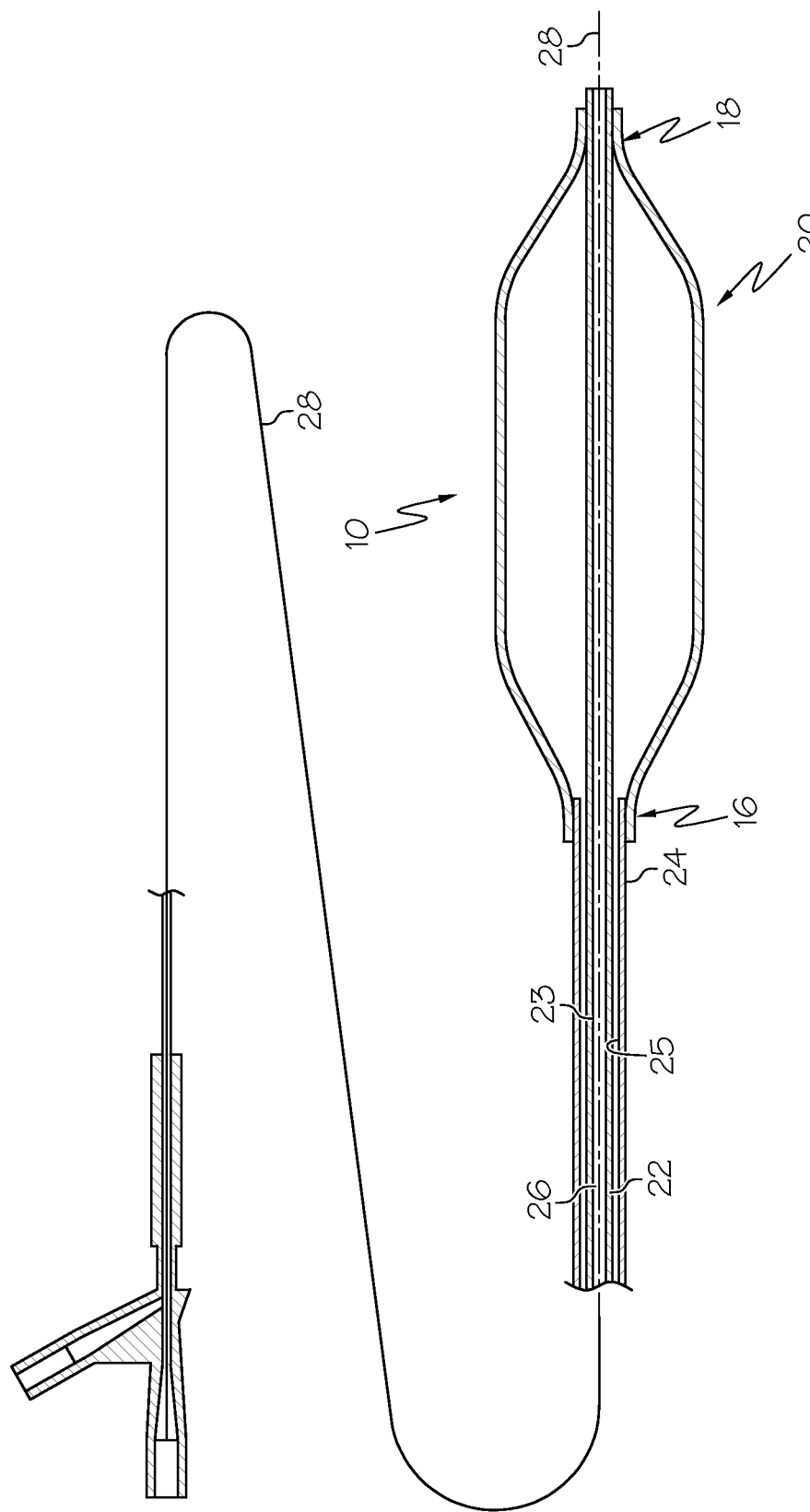
FIG. 4 is a longitudinal cross-section of a catheter assembly equipped with a balloon according to the invention.

FIG. 4 is a longitudinal cross-section of a catheter assembly 20 equipped with a balloon 10 according to the invention. Catheter assembly 20 is a dual-lumen catheter having an inner shaft 22 and an outer shaft 24. Inner shaft 22 has an inner surface 23 defining a guide wire lumen 26. Guide wire 28 is shown disposed within lumen 26.

Proximal waist 16 of balloon 10 is disposed about the distal end of outer shaft 24 and distal waist 18 of balloon 10 is disposed about the distal end of inner shaft 22.

Figure 5:
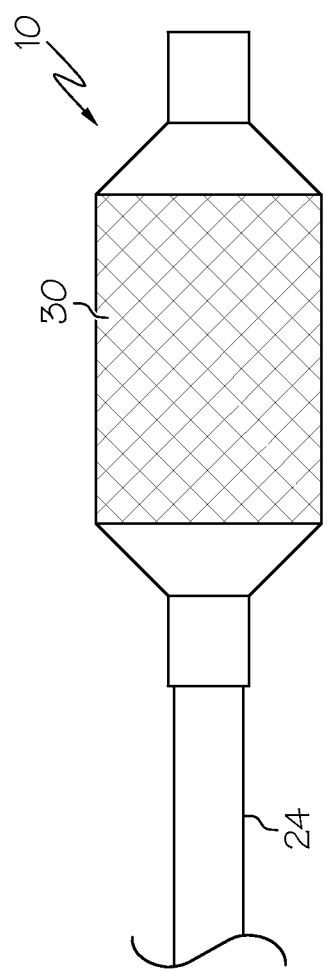
FIG. 5 is a side view of an expandable medical balloon with a stent disposed thereon.

The assembly may further incorporate a stent 30 disposed about balloon 10 as shown in FIG. 5. In the case of stent delivery application, it may be desirable to have a lubricious coating applied to only the waist portions 16, 18, cone portions 17, 19, or a combination of the waist and cone portions.

The balloons described herein may be employed in any of a variety of medical procedures including, but not limited to, angioplasty (PTCA) procedures, for delivery of medical devices such as stents (SDS), genito-urinary procedures, biliary procedures, neurological procedures, peripheral vascular procedures, renal procedures, etc.

The following non-limiting examples further illustrate some aspects of the present invention.

EXAMPLES

Example 1

Vestamid L2101F and Pebax 7033 were coextruded axially into the tubing of ID 0.0196 by OD 0.0348 inches. The outer layer was Vestamid L2101F with 70% of cross section area (material ratio) and the inner layer was Pebax 7033 with 30% of cross section area (material ratio). The tube was stretched at the speed of 50 mm/sec at 45° C. temperature with the inside pressure of 400 psi at a stretch ratio of 3.50. The stretched tube was inserted into a 0.1260 inch balloon mold (inner diameter or ID or balloon mold), and a balloon was formed at 95° C. and heat set right after formation at 120° C. for 1 minute. The balloon forming pressure was 500 psi.

The average balloon burst at 465 psi (31.6 atm) (burst pressure) with the average double wall thickness of 0.00114 inches. The average distention of the balloon was 5.8% at 6/16 atm range. The average balloon diameter was 3.3024 mm.

Burst strength is calculated using the following formula:

$$Strength = P \times D/2t$$

where P=internal pressure when the balloon bursts (kg/cm$^2$) (psi); D is the exterior diameter (mm) of the balloon when a pressure of 6.2 kg/cm$^2$ (88 psi) is applied; and t is the wall thickness of the portion of the balloon with the larger exterior diameter.

The calculated burst strength was 53,033 psi.

Hoop ratio can also be calculated using the following formula:

$$ID(BM)/(OD-ID) \times (\ln(OD/ID)) = \text{Hoop Ratio}$$

ID (BM) is the inner diameter of the balloon mold and OD and ID are the outer diameter and the inner diameter of the tubular parison respectively.

For example 1, the hoop ratio is 4.758.

Comparative Example A

For comparison, the same material ratio was used as described in the above example but with opposite material arrangement, i.e., the softer material outside. In this example, Vestamid L2101F is inner layer (70% in material ratio) and Pebax 7033 was outer layer (30% in the ratio). The same dimension tubing was extruded and the same size balloon was formed per balloon forming process described in the above example.

The tube was axially stretched at the speed of 50 mm/sec at 45° C. temperature with the inside pressure of 400 psi at a stretch ratio of 3.50. The stretch ratio is based on the starting length of the tube, X. In other words, the stretch ratio is 3.50X. The stretched tube was inserted into a 0.1260 inches balloon mold, and a balloon was formed at 95° C. and heated set right after formed at 120° C. for 1 minute. The balloon forming pressure was 500 psi.

The balloon burst at 386 psi (26.3 atm, in average) (burst pressure) with the average double wall thickness of 0.00108 inches. The distention of the balloon was 6.7% at 6/16 atm range. The average balloon diameter was 3.360 mm.

The calculated burst strength was 47,280 psi.

Comparative Example B

The same inner and outer layers were employed as in Example 1 but a different tubing stretch ratio was employed.

The tube was axially stretched at the speed of 50 mm/sec at 45° C. temperature with the inside pressure of 400 psi at stretch ratio of 4.25. The stretched tube was inserted into a 0.1260 inches balloon mold, and a balloon was formed at 95° C. and heat set right after formed at 120° C. for 1 minute. The balloon forming pressure was 600 psi.

The average balloon burst at 366 psi (24.9 atm) with the average double wall thickness of 0.00103 inches. The average distention of the balloon was 6.0% at 6/16 atm range. The average balloon diameter was 3.3505 mm.

The calculated burst strength was 46,872 psi.

Comparative Example C

The same inner and outer layers were employed as in Example 1 but a different heat set temperature was employed.

The tube was stretched at the speed of 50 mm/sec at 45° C. temperature with the inside pressure of 400 psi at stretch ratio of 3.50 (the same stretch ratio as in example 1). The stretched tube was inserted into a 0.1260 inches balloon mold, and a balloon was formed at 95° C. and heat set right after formed at 140° C. for 1 minute. The balloon forming pressure was 500 psi.

The average balloon burst at 391 psi (26.6 atm) (burst pressure) with the average double wall thickness of 0.00113 inches. The average distention of the balloon was 6.8% at 6/16 atm range. The average balloon diameter was 3.362 mm.

The calculated burst strength was 45,802 psi.

Increasing the heat set temperature to 140° C., was therefore found to have a negative impact on the burst pressure wherein a decrease of greater than 15% was seen over example 1. The corresponding drop in calculated burst strength was found to be greater than 10% over example 1.

The above disclosure is intended to be illustrative and not exhaustive. This description will suggest many variations and alternatives to one of ordinary skill in this art. The various elements shown in the individual figures and described above may be combined or modified for combination as desired.

The invention claimed is:

1. An expandable medical balloon comprising:
   an inner layer formed of a poly(ether-block-amide) copolymer; and
   an outer layer formed of a polyamide;
   the expandable medical balloon having a diameter of about 3.3 mm and a burst strength of greater than 45,000 psi.

2. The expandable medical balloon of claim 1 wherein said burst strength is greater than 47,500 psi.

3. The expandable medical balloon of claim 1 wherein said burst strength is greater than 50,000 psi.

4. The expandable medical balloon of claim 1 wherein said polyamide is formed from laurolactam.

5. The expandable medical balloon of claim 1 wherein said inner layer has a Shore D hardness of about 25D to about 70D.

6. The expandable medical balloon of claim 1 wherein said outer layer has a Rockwell hardness of about 60 to about 115.

7. The expandable medical balloon of claim 1 further comprising a lubricious coating on at least a portion of the outer layer.

8. The expandable medical balloon of claim 1 wherein said wall thickness of said balloon is about 10 microns to about 30 microns.

9. The expandable medical balloon of claim 8 further comprising a lubricious coating on at least a portion of the outer layer, said lubricious coating having a thickness of about 0.1 microns to about 2 microns.

10. The expandable medical balloon of claim 9, said lubricious coating having a thickness of about 0.5 to about 1 micron.

11. The expandable medical balloon of claim 1 wherein said inner layer provides at least about 10% of the burst strength of the resultant balloon.

12. The expandable medical balloon of claim 1 wherein said balloon comprises waist portions, cone portions and a body portion, said cone portions and said body portions comprise said inner and outer layer.

13. An expandable medical balloon comprising:
an inner layer formed of a polymer material having a Shore D hardness of about 25 to about 70; and
an outer layer formed of a polymer material having a Rockwell hardness of about 60 to about 115;
the expandable medical balloon having diameter of about 3.3 mm and a burst strength of greater than 45,000 psi.

14. The expandable medical balloon of claim 13 wherein the burst strength is greater than 47,500 psi.

15. The expandable medical balloon of claim 13 wherein the burst strength is greater than 50,000 psi.

16. The expandable medical balloon of claim 13 wherein said inner layer is formed of a polymer material having a Shore D hardness of about 50 to about 70.

17. The expandable medical balloon of claim 13 wherein said inner layer provides at least about 10% of the burst strength of the resultant balloon.

18. An expandable medical balloon comprising:
an inner layer formed of a poly(ether-block-amide) copolymer; and
an outer layer formed of a polyamide;
the inner layer is about 30% of the material area in cross-section and the outer layer is about 70% of the material area in cross-section of the balloon and the balloon having a burst strength of greater than 45,000 psi.

19. An expandable medical balloon comprising:
an inner layer formed of a poly(ether-block-amide) copolymer; and
an outer layer formed of a polyamide;
the expandable medical balloon having a burst strength of greater than 45,000 psi.

* * * * *